US00PP33395P2

(12) United States Plant Patent
Van Swieten

(10) Patent No.: US PP33,395 P2
(45) Date of Patent: Aug. 24, 2021

(54) ***PHALAENOPSIS* ORCHID PLANT NAMED 'PHALIEWE'**

(50) Latin Name: ***Phalaenopsis* hybrid**
Varietal Denomination: PHALIEWE

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,113

(22) Filed: Mar. 10, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALIEWE', particularly characterized by white, striped flowers with white and purplish-red, striped lips, a flat flower shape in lateral view, an incurving curvature of the longitudinal axis of the petal, and is propagated by meristem tissue culture, is disclosed.

3 Drawing Sheets

Genus and species: *Phalaenopsis* hybrid.
Variety denomination: 'PHALIEWE'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALIEWE'.

The new *Phalaenopsis* plant is a product of a planned breeding program conducted by the inventor in Bleiswijk, the Netherlands. The objective of this breeding program was to create a new *Phalaenopsis* plant with white, striped flowers with white and purplish-red, striped lips, suitable for potted plant production.

The new *Phalaenopsis* plant 'PHALIEWE' is a result of cross-pollination made by the inventor in April 2012 in Bleiswijk, the Netherlands, of the proprietary female, or seed parent, *Phalaenopsis* hybrid 'PHALBUKCAP' (U.S. Plant Pat. No. 25,445) with the proprietary male, or pollen parent, *Phalaenopsis* hybrid '29796-02' (unpatented).

The new *Phalaenopsis* was selected by the inventor as a single plant within the progeny of the stated cross-pollination in a controlled greenhouse in Bleiswijk, the Netherlands, in February 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 19, 2019 (Application no. 2019/2296), by Applicant who obtained the subject matter disclosed directly from the inventor. 'PHALIEWE' has not been made publicly available or sold anywhere in the world prior to the effective filing date of this application with the exception of sales or disclosures made one year or less before the effective filing date of this claimed invention by Applicant who obtained 'PHALIEWE' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALIEWE' as a new and distinct variety of *Phalaenopsis* plant:

1) White, striped flowers with white and purplish-red, striped lips;
2) Flower shape in lateral view is flat; and
3) Curvature of longitudinal axis of petal is incurving.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in January 2021. Colors in the photographs may differ from the color values cited in the detailed botanical description, which accurately describe the actual colors of the new variety.

DESCRIPTION OF THE NEW VARIETY

Figure 1:
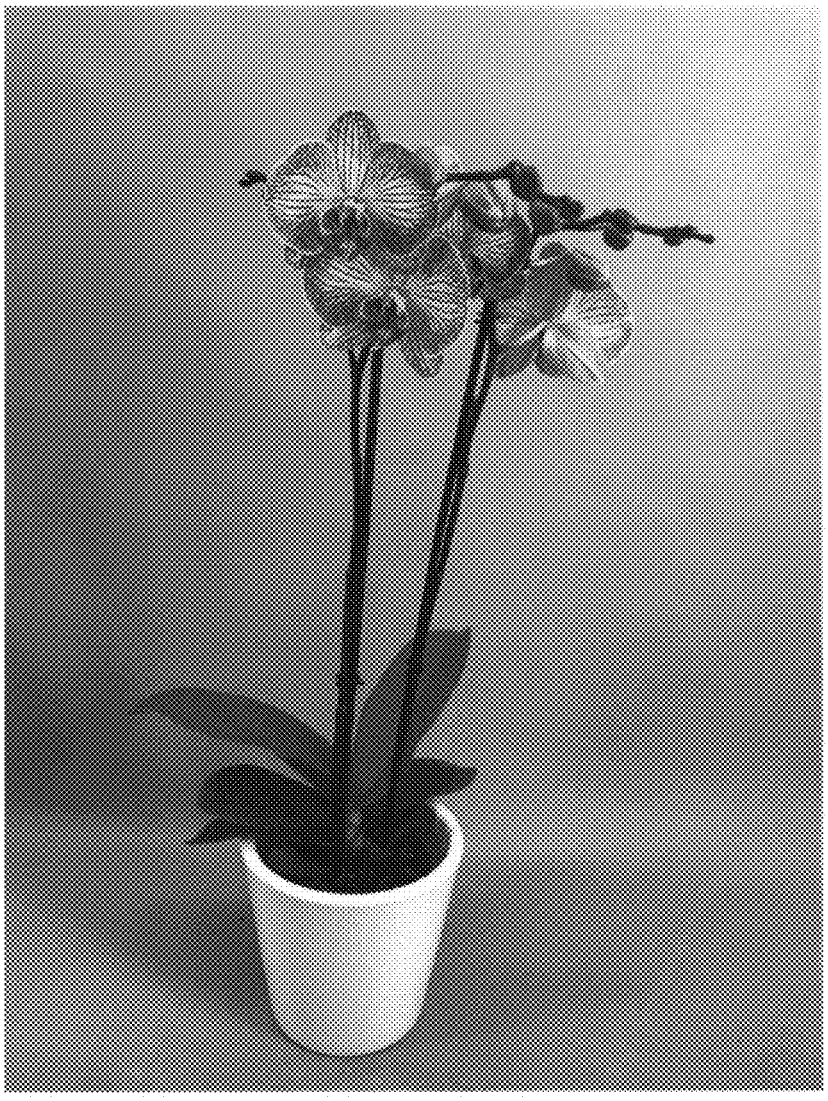
FIG. 1 shows the overall plant habit, including blooms, buds, and foliage of 'PHALIEWE'.
Figure 2:
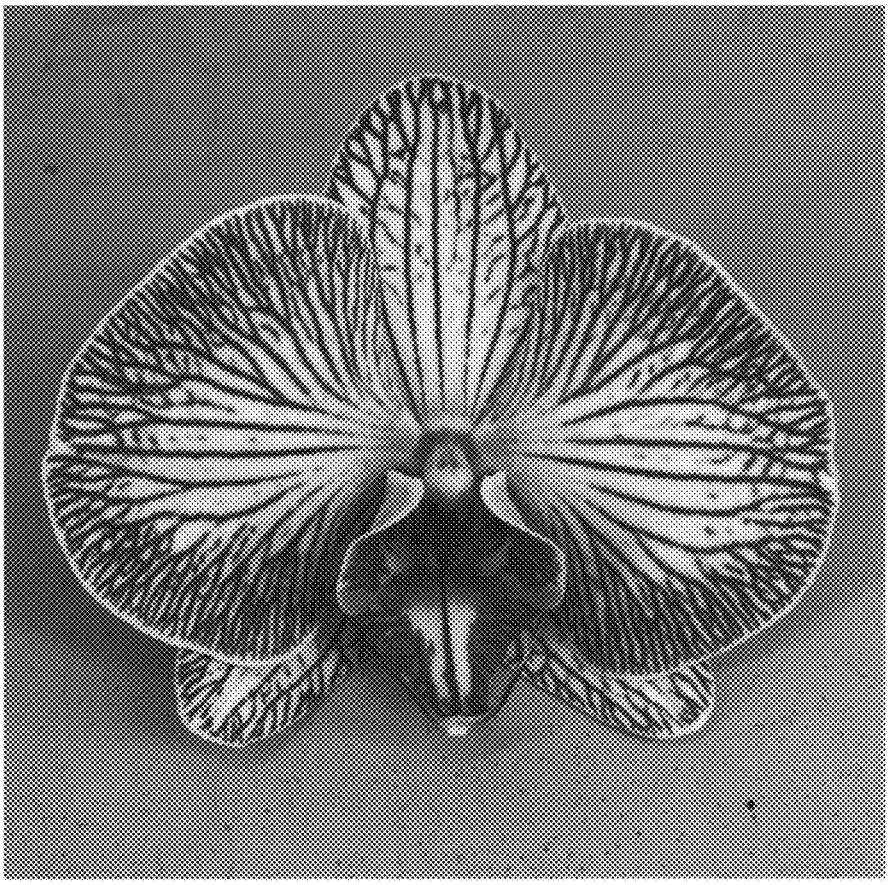
FIG. 2 shows a close-up of a flower of 'PHALIEWE'.
Figure 3:
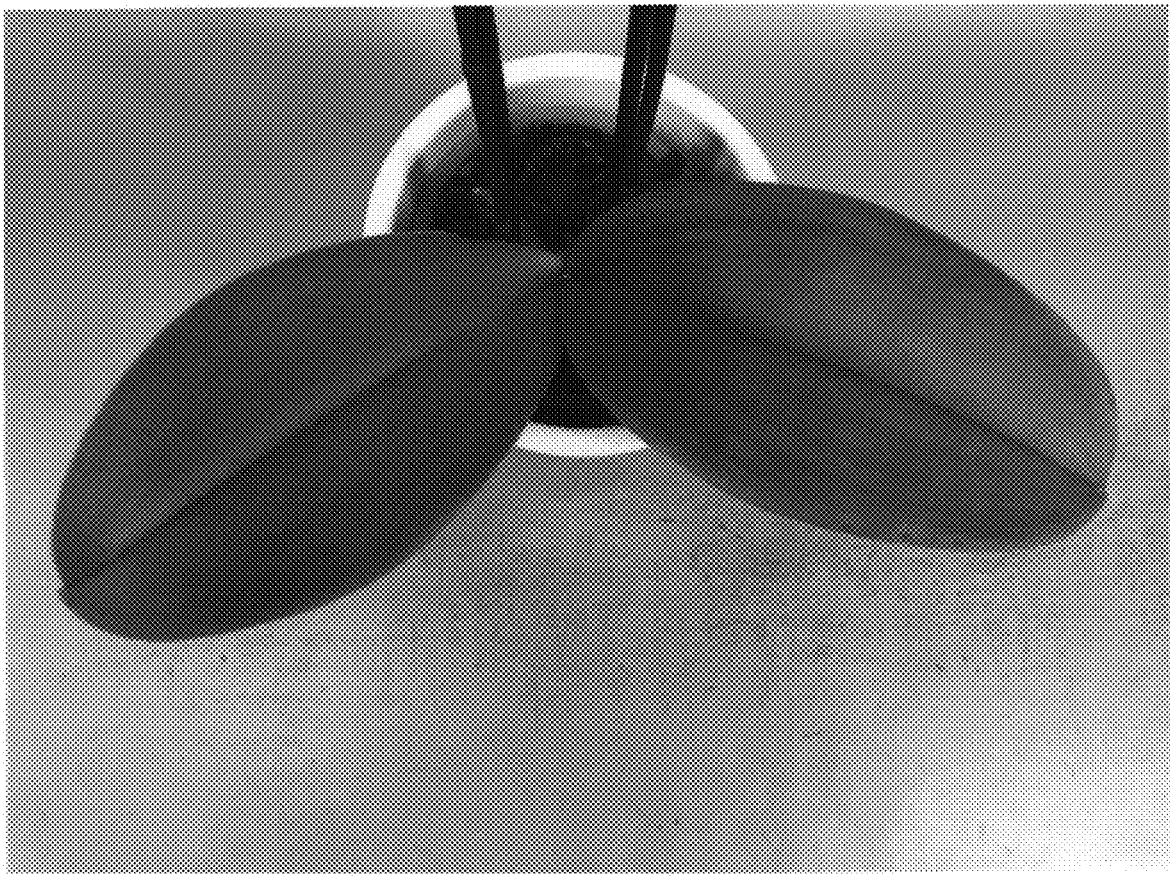
FIG. 3 shows an overhead view of the leaves of 'PHALIEWE'.

The following detailed description sets forth the distinctive characteristics of 'PHALIEWE'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in January 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHALIEWE'.

Parentage:
- *Female parent*.—*Phalaenopsis* cultivar 'PHALBU-KAP' (U.S. Plant Pat. No. 25,445).
- *Male parent*.—*Phalaenopsis* cultivar '29796-02' (unpatented).

Propagation:
- *Type*.—Meristem tissue culture.

Roots:
- *Root description*.—Greyed-green (a color in between RHS 190B and RHS 190C) colored roots with branching lateral roots having yellow-green (a color in between RHS 145B and RHS 145C) with a touch of RHS N78D colored root tips.

Plant:
- *Crop time to flowering*.—Following asexual propagation (in vitro), the rooted cuttings grow for 20-24 weeks. After transplantation into 12-cm pots, the plants are finished after 48 to 50 weeks.
- *Growth habit of the peduncle*.—Upright to slightly pendent with raceme and panicle inflorescence.
- *Height* (*from soil level to top of inflorescence*).—Approximately 50.0 cm to 55.0 cm.
- *Width* (*measured from leaf tips*).—About 26.0 cm to 29.0 cm.
- *Vigor*.—Strong.

Leaves:
- *Mature leaves*.—Quantity per plant: 6 to 8 leaves are produced before flowering. Length (fully expanded): 17.0 cm to 19.0 cm. Width: 8.0 cm to 9.0 cm. Position of the broadest part of the leaf: At the middle. Shape: Oblong. Base shape: Moderately elongated. Apex: Unequal obtuse. Leaf blade angle with the petiole (measured from the horizontal position): Between 15 degrees and 35 degrees. Leaf margin: Entire. Color: Upper surface: A color in between RHS 144A and RHS 146A. Lower surface: RHS 146B. Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146B.

Peduncle:
- *Quantity per plant*.—1 to 2.
- *Number of flowers per peduncle*.—8 to 12.
- *Length*.—50.0 cm to 55.0 cm.
- *Diameter*.—4.0 mm to 5.0 mm.
- *Strength*.—Strong.
- *Aspect*.—Upright to slightly pendent.
- *Texture*.—Smooth.
- *Color*.—Reddish-brown (a color in between RHS 187A and RHS 200B).
- *Internode length*.—3.0 cm to 4.0 cm.

Inflorescence description:
- *Appearance*.—Upright to slightly pendent, raceme and panicle inflorescence with bilaterally symmetrical flowers that open in succession beginning with the lowermost flower.
- *Number of inflorescences*.—1 to 2.
- *Inflorescence size*.—Height (from base to tip): 180.0 mm to 230.0 mm.
- *Flowering time*.—First flowers can be expected 10 to 11 months after planting in a 12-cm pot.
- *Flower*.—Height: 78.0 mm to 83.0 mm. Diameter: 90.0 mm to 95.0 mm. Depth of lip: 25.0 mm to 27.0 mm.
- *Flower longevity*.—On the plant: 11 to 13 weeks.
- *Flower shape*.—Flat.
- *Fragrance*.—Absent.
- *Flower bud*.—Average size: Medium to large. Length: 21.0 mm to 23.0 mm. Width: 17.0 mm to 19.0 mm. Shape: Egg shaped. Color: Light yellow-green (RHS 145C); purplish-red (RHS N77B) and diluting dark purplish-red stripes (RHS N79B).
- *Petals*.—Arrangement: Open/free. Shape: Semi-circular. Apex: Emarginated to rounded asymmetric. Margin: Weakly undulated. Length (from base to tip): 44.0 mm to 46.0 mm. Width: 56.0 mm to 58.0 mm. Position of the broadest part of the petal: Toward the base. Color (when fully opened): Upper surface: Basic color: White (RHS NN155C). Over color: Touch of very reddish-purple (RHS N78B) at the base; reddish-purple stripes (RHS N78A and RHS N78C). Lower surface: Basic color: White (RHS NN155C). Over color: Very light purple shade (RHS 76B) and purplish-pink stripes (RHS N78C and RHS N78A). Number of spots and stripes on the petals (upper surface): Many stripes. Color of spots and stripes on the petals (upper surface): RHS N78A. Density of netting of the petals (upper surface): None. Color of the netting (upper surface): Not applicable.
- *Dorsal sepal*.—Shape: Elliptic. Apex: Obtuse symmetric. Margin: Entire. Length (from base to tip): 44.0 mm to 46.0 mm. Width: 30.0 mm to 32.0 mm. Position of the broadest part of the dorsal sepal: At the middle. Color (when fully opened): Upper surface: Basic color: White (RHS NN155C). Over color: Hint of purplish-pink (RHS N78C) at the base; reddish-purple stripes and netting (RHS N78A). Lower surface: Basic color: Light purple (a color in between RHS 76A and RHS 76B). Over color: Light yellow-green (RHS 145C); diluting stripes (RHS N78A and RHS N78C). Number of spots and stripes on the dorsal sepals (upper surface): Medium stripes.

Color of spots and stripes on the dorsal sepals (upper surface): RHS N78A. Density of netting of the dorsal sepals (upper surface): Low to medium. Color of the netting (upper surface): RHS N78A.

*Lateral sepals*.—Shape: Ovate. Apex: Obtuse symmetric. Margin: Entire. Length (from base to tip): 44.0 mm to 46.0 mm. Width: 27.0 mm to 29.0 mm. Position of the broadest part of the lateral sepal: At the base. Color (when fully opened): Upper surface: Basic color: White (RHS NN155C). Over color: Light yellow-green (RHS 145C); dotted (RHS 71A); reddish-purple stripes and netting (RHS N78A). Lower surface: Basic color: Very light purple (RHS 76B). Over color: Light yellow-green (a color in between RHS 145C and RHS 145D); diluting purplish-pink stripes (RHS N78C); reddish-purple midvein (RHS 184D) toward the tip. Number of spots, dots, and stripes on the lateral sepals (upper surface): Medium stripes and few dots. Color of spots, dots, and stripes on the lateral sepals (upper surface): Stripes (RHS N78A); dots (RHS 71A). Density of netting of the lateral sepals (upper surface): Low to medium. Color of the netting (upper surface): RHS N78A.

*Labellum* (*lip*).—Whiskers: Present. Length of whiskers: 15.0 mm to 17.0 mm. Color of whiskers: Dark purplish-red (RHS N79B) with white margins and tips (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 21.0 mm to 23.0 mm. Width: 15.0 mm to 17.0 mm. Color: Upper surface: White (RHS NN155C) and striped (RHS 187C) at the base; greenish-yellow (RHS 6A) toward margin on one side; white margin (RHS NN155C) on the other side; reddish-purple stripes (RHS N78A) toward the tip. Lower surface: White (RHS NN155C); greenish-yellow (RHS 3A) toward margin on one side; light purple shade (RHS 76A); reddish-purple stripes (RHS N78A and RHS N78B). Number of spots and stripes on the lateral lobe: Many stripes. Color of spots and stripes on the lateral lobe: RHS 187C and RHS N78A. Density of netting of the lateral lobe: None. Color of the netting: Not applicable.

*Apical lobe*.—Shape: Triangular. Margin: Entire. Length: 21.0 mm to 23.0 mm. Width: 26.0 mm to 28.0 mm. Color: Upper surface: Greenish-yellow (RHS 3B) at the base and toward wings; white (RHS NN155C) at the middle from base toward whiskers; purplish-red (RHS N78A); dark purplish-red midvein and stripes (RHS N79C) toward margins. Lower surface: White (RHS NN155C) at the middle from base toward whiskers; greenish-yellow wings (RHS 3B); reddish-purple stripes (RHS N78A) toward margins on both sides. Number of spots and stripes on the apical lobe: Few to medium. Color of spots and stripes on the apical lobe: RHS N78A. Density of netting of the apical lobe: None. Color of the netting: Not applicable.

*Callus*.—Average size: Medium to large. Height: 8.0 mm to 9.0 mm. Length: 5.0 mm to 6.0 mm. Width: 5.0 mm to 6.0 mm. Color: Yellow (RHS 9C); dotted (RHS 59B).

Reproductive organs:

*Column*.—Length: 8.0 mm to 10.0 mm. Diameter: 5.0 mm to 6.0 mm. Color: Light purple (RHS 76A) with reddish-purple stripe (RHS N78B) at the middle toward the tip.

*Pollinia*.—Quantity: 2. Diameter: 0.9 mm to 1.1 mm. Color: Orange (RHS 24A).

*Ovary*.—Length: 11.0 mm to 13.0 mm. Diameter: 2.3 mm to 2.6 mm.

*Pedicel*.—Length: 34.0 mm to 36.0 mm. Diameter: 2.8 mm to 3.0 mm. Color: Touch of reddish-brown (RHS 176B) at the base; yellow-green (a color in between RHS 145B and RHS 145C); light reddish-purple (RHS N78D) and light purple (RHS 76B) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALIEWE' differs from the female parent plant 'PHALBUKAP' (U.S. Plant Pat. No. 25,445) in that 'PHALIEWE' has oblong leaves and petals with an incurving curvature of the longitudinal axis, whereas 'PHALBUKAP' has narrow obovate leaves and petals with a recurving curvature of the longitudinal axis.

'PHALIEWE' differs from the male parent plant '29796-02' (unpatented) in that 'PHALIEWE' has obtuse dorsal sepal apexes and light purple columns with a reddish-purple stripe at the middle, whereas '29796-02' has emarginated dorsal sepal apexes and reddish-purple columns. Additionally, 'PHALIEWE' has longer whiskers than '29796-02'.

'PHALIEWE' is most similar to the commercial *Phalaenopsis* plants named 'PHALFESFI' (U.S. Plant Pat. No. 31,481) and 'PHALBUKALO' (U.S. Plant Pat. No. 28,322). 'PHALIEWE' differs from the commercial variety 'PHALFESFI' in that 'PHALIEWE' has emarginated to rounded petal apexes and light purple columns with a reddish-purple stripe at the middle, whereas 'PHALFESFI' has obtuse petal apexes and light reddish-purple columns with a reddish-purple region toward the tips. Additionally, 'PHALIEWE' has a larger depth of lip than 'PHALFESFI'.

'PHALIEWE' differs from the commercial variety 'PHALBUKALO' in that 'PHALIEWE' has obtuse dorsal sepal apexes, a medium curvature of the lateral lobe, and low to medium netting on the lateral sepals, whereas 'PHALBUKALO' has rounded dorsal sepal apexes, a weak curvature of the lateral lobe, and high to very high netting on the lateral sepals.

I claim:

1. A new and distinct variety of *Phalaenopsis* plant named 'PHALIEWE', substantially as described and illustrated herein.

* * * * *